United States Patent
Alvarez Hernandez

(10) Patent No.: US 6,419,905 B1
(45) Date of Patent: Jul. 16, 2002

(54) TOOTH WHITENING COMPOSITION

(75) Inventor: Maria Alvarez Hernandez, Madrid (ES)

(73) Assignee: Biocosmetics, S.L., Madrid (ES)

(*) Notice: Subject to any disclaimer, the term of this patent is extended or adjusted under 35 U.S.C. 154(b) by 0 days.

(21) Appl. No.: 09/646,659

(22) PCT Filed: Mar. 18, 1999

(86) PCT No.: PCT/ES99/00070

§ 371 (c)(1),
(2), (4) Date: Nov. 17, 2000

(87) PCT Pub. No.: WO99/48467

PCT Pub. Date: Sep. 30, 1999

(30) Foreign Application Priority Data

Mar. 20, 1998 (ES) .................................. 9800598

(51) Int. Cl.$^7$ ............................. A61K 7/20; A61K 7/18; A61K 7/16

(52) U.S. Cl. ............................ 424/53; 424/49; 424/52

(58) Field of Search ................................ 424/49–55, 53

(56) References Cited

U.S. PATENT DOCUMENTS

| | | | | |
|---|---|---|---|---|
| 3,901,819 A | * | 8/1975 | Nakagawa et al. | 252/186 |
| 4,980,152 A | * | 12/1990 | Frazier et al. | 424/53 |
| 5,089,255 A | * | 2/1992 | Gaffar et al. | 424/52 |
| 5,122,365 A | * | 6/1992 | Murayama | 424/49 |
| 5,151,212 A | * | 9/1992 | Bell et al. | 252/186.38 |
| 5,211,559 A | * | 5/1993 | Hart et al. | 424/52 |
| 5,256,402 A | * | 10/1993 | Prencipe et al. | 424/53 |
| 5,718,886 A | * | 2/1998 | Pellico | 424/53 |
| 5,766,574 A | * | 6/1998 | Christianbeck et al. | 424/53 |
| 5,851,512 A | * | 12/1998 | Fischer | 424/49 |
| 5,855,870 A | * | 1/1999 | Fischer | 424/49 |
| 5,891,452 A | | 4/1999 | Sebillote-Arnaud et al. | |
| 5,891,453 A | * | 4/1999 | Sagel et al. | 424/53 |
| 5,928,628 A | * | 7/1999 | Pellico | 424/53 |
| 5,985,249 A | * | 11/1999 | Fischer | 424/53 |
| 6,036,943 A | * | 3/2000 | Fischer, IV | 424/49 |
| 6,096,328 A | * | 8/2000 | Sagel et al. | 424/53 |
| 6,136,297 A | | 10/2000 | Sagel et al. | |

FOREIGN PATENT DOCUMENTS

| | | | |
|---|---|---|---|
| ES | 2079325 | | 1/1996 |
| GB | 1267618 | * | 3/1972 |
| WO | WO 97/04742 | | 2/1997 |
| WO | WO 99/48467 | | 9/1999 |

* cited by examiner

*Primary Examiner*—Shep K. Rose
(74) *Attorney, Agent, or Firm*—Katten Muchin Zavis Rosenman

(57) ABSTRACT

The composition contains carbamide peroxide (0.3–60%), xylitol (0.5–50%) potassic salt (0.001–10%) and fluorine salt (0.15–3%). There is also disclosed a gel which contains, in addition to the whitening composition, between 0.5 and 6% by weight of an appropriate gelifying agent. The gel is appropriate to the whitening of dental pieces through a treatment which comprises applying an efficient amount of said whitening gel onto the dental pieces to be whitened. The composition may also be presented in the form of a dental paste, mouth wash or elixir.

7 Claims, No Drawings

TOOTH WHITENING COMPOSITION

SUMMARY

The composition comprises carbamide peroxide (0.3–60%), xylitol (0.5–50%), a potassium salt (0.001–10%) and a fluorine salt (0.15–3%). A gel is disclosed that contains, as well as the bleaching composition, between 0.5 and 6% by weight of an appropriate gelling agent. The gel is suitable for bleaching dental pieces by means of a treatment that comprises applying an effective quantity of said bleaching gel to the dental pieces to be bleached. The composition can also be presented in the form of a toothpaste, colutory or elixir.

1. Field of the Invention

This invention relates to a composition suitable for bleaching the teeth, based on carbamide peroxide as well as presentation formulations thereof

2. Background of the Invention

Dental discoloration, or loss of whiteness of dental pieces with subsequent appearance of stains thereon, is a complex process in which numerous and different causes may be implicated. Types of dental discoloration can be classified in accordance with the localisation and aetiology of the stains. Recent studies propose the classification of dental stains (extrinsic and intrinsic) according to the chemistry of the dental discoloration [Nathoo, S. A., "The chemistry and mechanism of extrinsic and intrinsic discoloration", JADA, 1997, 128:65–95]. According to this work, extrinsic dental stains, that is to say, those that are found on the surface of the dental pieces, are classified into the following groups:

(a) direct dental stains, that may be: (i) of N1 type, when the chromogen which binds to the dental surface to provoke the discoloration has a colour similar to that of the dental stain and may be due to the formation of a film of saliva that leads to fixing of components from the saliva by the dental enamel, to the ingestion of certain drinks and foods such as tea, coffee and wine, to bacterial adhesion and to the presence of metals in the oral cavity, or (ii) of type N2, when the chromogen changes colour after binding to the dental piece, due, for example, to the accumulation or chemical modification of proteins present in the film of saliva by means, for example, of denaturing with acids or detergents or else due to darkening, with the passage of time, of the dental stains of type N1 caused by drinks and foods; and (b) indirect dental stains, in which a transparent material (or pre-chromogen material) binds to the dental piece and undergoes chemical reaction that produces the stain Among the products that provoke this type of stain there can be found, for example, food products rich in carbohydrates and sugars as well as certain therapeutic agents, for example, tin fluoride.

The intrinsic discoloration of the dental pieces is due to the presence of chromogenic material within the enamel or dentin. This type of discoloration can be due, among other things, to a fluorosis provoked by an excessive ingestion of fluorine during dental development, to the administration of tetracycline during the years of tooth formation, to a congenital malformation of the dental tissue, to certain hematologic disorders (erythroblastosis fetalis, thalassemia), to cracks and breaks in the dental pieces, to haemorrhages in the dental pulp, and to the normal ageing process.

Different methods and systems are known for eliminating dental discoloration and for provoking the bleaching of the dental pieces that comprise the use either of abrasives, such as prophylactic pastes, or a combination of abrasives and surfactants, for example, whitening toothpastes. ES-B-2079325 discloses a bleaching toothpaste containing an abrasive system (silica) and a detergent (sodium laurylsarcosinate). The use of abrasives for whitening dental pieces is not recommendable as it may lead to the elimination of part of the dental enamel along with the stains themselves which would facilitate the appearance of tooth decay and erosions due too the elimination of the natural defensive structure of the enamel with the subsequent dental hyperesthesia.

A tooth whitening composition in the form of a gel is provided by U.S. Pat. No. 5,718,886, wherein it is disclosed a stabilized anhydrous tooth whitening gel composition comprising carbamide peroxide dispersed in an anhydrous gelatinous carrier, said carrier comprising a polyol, a thickener, and xanthan gum in order to stabilize the gel composition against viscosity degradation during oral use.

In general, said whitening methods avoid the accumulation, and, to a certain extent, eliminate extrinsic dental stains although total and satisfactory elimination of the dental stains depends on the type of discoloration. In general, the extrinsic stains of type N1 can be avoided or eliminated by means of good oral hygiene, while the extrinsic stains of type N2, which are more difficult to eliminate, require the skill of a professional for dental bleaching. This is also true for stains of type N3. On the other hand, the elimination of intrinsic dental stains requires the use of products that penetrate the enamel and dentin with the aim of discolouring and dissolving the chromogens responsible for these stains.

Dental discoloration occurs widely in society (it is estimated that two out of every three adults suffers from some type of dental discoloration). It produces a certain anti-aesthetic effect that can even inhibit the smile of people suffering from discoloration. The occurrence can become particularly important in certain situations and professions where showing clean and white teeth is essential.

There exists, therefore, the need to have a new medium suitable for eliminating dental stains and bleaching the dental pieces that overcomes the drawbacks mentioned hereinabove. This objective may be attained by means of the use of a bleaching composition provided by this invention whose use leads to a clearing up of the dental enamel, which thus starts to a acquire a whiter and more brilliant appearance.

DETAILED DESCRIPTION OF THE INVENTION

The invention provides a dental bleaching composition, hereinafter, composition of the invention, that comprises:

| Components | % by weight with respect to total |
| --- | --- |
| Carbamide peroxide | 0.3–60 |
| Xylitol | 0.5–50 |
| Potassium salt | 0.001–10 |
| Fluoride salt | 0.15–3 |

The carbamide peroxide is a mixture of hydrogen peroxide and carbamide whose amino groups neutralise the acidity of the hydrogen peroxide. This compound acts as an oxidative bleaching agent that liberates oxygen. It is able to oxidatively degrade numerous organic colouring agents present both in food products and in pharmaceutical products that produce dental colourings. In general, the organic colouring agents owe their dyeing capacity to the present of chromophor groups, that is to say, chemical groups rich in electrons, generally conjugated double bonds. Illustrative examples of organic colorants are, erythrosine, used as a developer for bacterial plaque, tartracine, used as a food additive, indigotine, used in the formulation of some drugs, and tetracycline, an antibiotic that produces dental colourings that range from yellow to brown. It is believed that oxidative degradation (oxidative bleaching) of this type of colorant occurs via a mechanism that implicates the decomposition of hydrogen peroxide and the formation of free radicals (HO—) that attack the double bonds present in the molecules of said colorants and, subsequently, produce the breakage of the double bonds and the oxidation of the carbons implicated to corresponding carbonyl groups. The carbonyl groups formed, although they also possess $\pi$ (Pi) electrons as in the C=C double bonds, absorb in the ultraviolet zone of the spectrum and so do not contribute to discoloration. Numerous studies show that the bleaching activity of the carbamide peroxide (see for example, Van B. Haywood, "History, safety and effectiveness of current bleaching techniques and applications of the nightguard vital bleaching technique", Quintessence Int. 23: 471–488 (1992); Howard E. Strassaler et al., "Carbamide Peroxide At-Home Bleaching Agents", The New York State Dental Journal, April 1992, 30–34; Van. B. Haywood, "Night Guard vital bleaching: Effects of various solutions on enamel surface texture and colour", Quintessence Int. 22: 775–782 (1991); and Van B. Haywood, "Situación actual del blanquemiento dental mediante cubetas", Journal of Aesthetic Dentistry, Ed. Española, 2: 10–15 (1992)].

Xylitol (1,2,3,4,5-pentapentol) is a natural sweetener that reduces the dental plaque and has activity as an inhibitor of tooth decay. This polyalcohol, due to its molecular size, helps to complex the formulation and, furthermore, contributes to making the solution more alkaline and so it would not be absolutely necessary to incorporate other alkalinising agents.

As a potassium salt, any salt may be used that releases potassium ions in a suitable quantity. The potassium acts as a desensitiser in cases of dental hypersensitivity. Illustrative examples, not limiting, of potassium salts that may be used in the composition of the invention include potassium citrate (including tripotassium citrate), potassium fluoride, potassium benzoate, potassium bicarbonate, potassium carbonate, potassium chloride, potassium lactate, potassium pyrophosphate, potassium phosphate, and mixtures thereof, preferably potassium citrate.

The fluorine salt is a salt able to release fluoride ions in a suitable quantity. By way of example for illustrative purposes, and not limiting, said fluorine salt may be a fluoride of a alkaline metal, for example, sodium fluoride, potassium fluoride, sodium monofluorophosphate, di-potassium hexafluorosilicate, and mixtures thereof, preferably, potassium fluoride. The fluoride acts as a re-mineralising agent of the enamel. The inclusion of fluoride in the composition of the invention reduces the losses of said ion that are produced during the bleaching actions.

The composition of the invention may be prepared by mixing and homogenising the different components in suitable quantities.

The composition of the invention may be present in different presentation formulations, including formulations of solid or semi-solid administration, for example, toothpastes, liquids, for example, colutories or elixirs; or gels; for which the additives are incorporated, suitable vehicles and excipients for processing thereof in the desired presentation formulation. These presentation formulations of the composition of the invention can be easily prepared by means of the use of conventional techniques [Tratado de Farmacia Galénica, C. Fualí I Trillo, Luzán 5 S. A. de Ediciones, $1^{st}$ Edition, (1993), especially chapters 35, 47 and 59; Cosmetología Teérico-Práctica, published by the Consejo General de Colegios Oficiales de Farmacéuticos, $3^{rd}$ Edition (1985), Chapter 7].

In a particular and preferred embodiment of this invention the formulation of presentation of the composition of the invention is a gel. In this case, in the composition of the invention a suitable gelling agent is introduced, such as a natural or synthetic polymer, in an appropriate amount to form a tri-dimensional matrix in the solution or suspension to be gelled. The gelling agent is selected from a group formed by a carboxyvinyllic polymer, a co-polymer of polyoxyethylene and polypropylene, and mixtures thereof In a particular embodiment, the gelling agent is a synthetic polymer that gives rise to a gel depending on the pH of the medium, such as a carboxyvinyllic polymer or a vinyl polymer that contains active carboxyl groups [The Merck Index, $11^{th}$ Edition, 1989, Merck & Co., Inc., Rahway, N.J., United States, page 278, Monograph no. 1836] that produces the gelling of solutions and suspensions by neutralisation with a base. Examples of carboxyvinyllic polymers are those conmmercialised with the tradename Carbopol® (The B.F. Goodrich), that produce gels of varying viscosity depending, among other things, on the type of Carbopol® used (Carbopol® 940, Carbopol® 934) and the pH of the medium. Other gelling agents that can also be used are polyvinylpyrrolidone (polymer of N-vinylpyrrolidone), the polymers of polycarboxylates, for example, those conmmercialised with the denomination Gantrez ACV-4006, and the co-polymers of polyoxyethylene and polyoxypropylene such as those known as poloxamers or Pluronics (Pluronic F127, F108 and F98). The gelling agent can be present in the gel composition in an amount lying between 0.5 and 6% by weight with respect to the total of the composition.

The incorporation of the gelling agent also allows slow release of the carbamide peroxide present in the composition of the invention thus taking fuller advantage of its bleaching effect.

The gel provided by this invention, hereinafter the bleaching gel of the invention, has a pH approximately neutral and can have a carbamide peroxide content lying between 0.3 and 60% by weight with respect to the total, preferably, between 3 and 50% by weight with respect to the total. The gels that contain between 3 and 6% by weight of carbamide peroxide are particularly suitable for use in the daily brushing of teeth in combination with a whitening toothpaste that contains, advantageously, the composition of the invention, while the gels that contain between 10 and 15% by weight of carbamide peroxide are suitable for use in daily brushing of teeth and for topical application to the dental pieces. Finally, gels that contain between 20 and 50% by weight of carbamide peroxide are suitable for topical application to dental pieces. Topical application of the gets provided by this invention may be effected with the help of a suitable instrument, such as a brush or a dental spatula.

The bleaching gel of the invention may also contain other appropriate additives such as alkalinising agents, aromatising agents, sweeteners, thickeners and moisteners that assist in adjusting the pH, improve the organoleptic characteristics and/or conditions of elaboration. They may be those typically used in the sector of the art Such additives can be conventional additives regularly used in this sector of the art.

By way of example, alkalinising agents can be mentioned such as sodium hydroxide or triethanolamine, although the alkalinising power of the latter of these may by substituted modifying the amount of potassium salt present in the composition or even by the alkalinising power of xylitol; sweeteners such as saccharine or derivatives of cyclamic acid; thickeners such as triethanolamine, derivatives of starch, xanthane gum, colloidal silicas and similar substances; and moisteners, such as glycerine. Each one of the alkalinising additives, aromatising agents, sweeteners and thickeners can be present in the composition of gel in an amount lying between 0 and 6% by weight with respect to the total of the composition, while the moistener may be present in an amount lying between 40 and 80% by weight with respect to the total of the composition.

In a specific preferred embodiment of the invention, there is provided a bleaching gel that has the following composition:

| Components | % by weight, with respect to total |
| --- | --- |
| Carbamide peroxide | 0.3–60 |
| Xylitol | 0.5–50 |
| Potassium salt | 0.001–10 |
| Fluoride salt | 0.15–3 |
| Gelling agent (1) | 0.5–6 |
| Triethanolamine | 0.1–6 |
| Aroma | 0.5–6 |
| Saccharine | 0.1–6 |
| Glycerine | 45–75 |

(1) Preferably, the gelling agent is a carboxyvinyllic polymer that contains active carboxyl groups of the type of those commercialised with the trademark Carbopol ®.

(1) Preferably, the gelling agent is a carboxyvinyllic polymer that contains active carboxyl groups of the type of those commercialised with the tradename Carbopol®.

The bleaching gel of the invention can be used to bleach dental pieces. Therefore, the invention also provides a method for bleaching dental pieces that comprises the use of the bleaching gel of the invention.

In a particular embodiment of the invention, the bleaching method of the dental pieces provided by this invention can by carried out using a bleaching gel of the invention that contains between 10 and 15% by weight, preferably, 12% by weight, of carbamide peroxide. Said method comprises preparing a splint that may be placed over the dental pieces to be bleached, applying the bleaching gel to the inside of the splint and placing the splint with the bleaching gel over the dental pieces to be bleached.

The preparation of the splint may be carried out by any conventional method, for example, taking an impression in alginate of the teeth or dental pieces to be bleached, preparing a model in plaster and constructing the splint from a tablet of flexible resin. The bleaching gel of the invention is applied to the inside of the splint, either by means of some drops, or forming a line, and then, the splint loaded with bleaching gel is placed over the teeth or dental pieces to be bleached and is worn for the time the specialist considers opportune, normally between 3 and 4 weeks. This splint, loaded with bleaching gel, can be worn for during the day, during the night, in the user's own home, or both day and night.

In an alternative embodiment, the invention provides a method for bleaching dental pieces using a bleaching gel of the invention that contains between 20 and 50% by weight, preferably, 30% by weight, of carbamide peroxide. This method is effected in the practice or dental clinic and comprises (a) applying the bleaching gel to the external face of the teeth or dental pieces to be bleached with the aid of a suitable instrument, such as a brush or a dental spatula, keeping the lips apart using a soft-tissue extractor or with rolls of cotton, and (b) allowing the gel to act for a suitable period of time, lying between 15 and 30 minutes, normally 20 minutes. By means of carrying out this alternative it is possible to possible to bleach to a middle tone or several teeth between 15 and 30 minutes. This method can be carried out as the start of treatment with a splint or to accelerate this process, with application is sessions of 15 to 30 minutes once a week.

The tests carried out have shown that:
application of the bleaching gel of the invention does not require the use of gum protectors or lip protectors
the results depend on the duration of the treatment and on the number of hours that the gel is used daily,
it can be applied nocturnally and/or during the day according to the requirements of each person,
it supplies the inner tooth with oxygen,
it improves the gingival health
the novel supply of fluorine makes the appearance of post-bleaching sensitivity almost non-existent and, therefore, it is more agreeable to the user;
The novel inclusion of xylitol means that the duration of the bleaching process also provides an anti-tooth decay effect
the release of potassium, both by the potassium fluoride and by the potassium citrate, means that in the case of very sensitive teeth the duration of the bleaching process also provides a blockade of the sensitivity thanks to the potassium; and
it is especially indicated in the bleaching of teeth yellowed or stained by tetracyclines (moderate stains), tobacco, ageing and fluorosis.

Different tests have also demonstrated that the time necessary for dental bleaching using the gel provided by this invention, depends, among other things, on the initial discoloration and on the carbamide peroxide concentration present in the bleaching gel, reducing the time needed for dental bleaching.

In another particular embodiment of this invention, the presentation formulation of the composition of the invention is a toothpaste, for which, the conventional appropriate additives and excipients are introduced into the composition of the invention to improve its properties and characteristics and for facilitating its processing, such as abrasives, binding agents, aromatising agents, colorants, preservatives, sweeteners, thickeners, moisteners, lubricating agents, clouding agents, re-mineralisers, flavourings, buffers (pH regulators), surfactants and vitamins, regularly used in this sector of the art for the formulation of toothpastes The toothpaste, if so desired, may also incorporate up to 0.5% by weight of a gelling agent of the type described previously in relation to the bleaching gel of the invention.

The abrasive may a system based on silica that comprises a mixture of viscosing silica and abrasive silica. The binding agent may be, for example, tragacanth gum. As an aromatising agent, colorant and flavouring any of those regularly used in the formulation of toothpastes may be used, for example, mint aroma and Brilliant blue FCF, CI.42090 (KIRSCH PHARMA). The preservative may be a benzoic acid derivative, for example, methyl p-hydroxy-benzoate. As a sweetener substances that may be used include, for example, sodium saccharine or cyclamic acid and derivatives thereof, for example sodium cyclamate. The thickener may be, for example, derivatives of starch, xanthane gum, or colloidal silicas. As a moistener glycerine may be used for example, although xylitol also may act as a moistener. The lubricant may be, for example, dimethicone (polymer of dimethylpolysiloxane), which is a surfactant that contributes to conferring good Theological properties on the toothpaste provided by this invention. The clouding agent may be, for example, titanium dioxide. As a re-mineralising agent a source of fluoride may be used. As a buffer any of those regularly used may be employed that gives the desired pH. The vitamins that, optionally, may be present in the toothpaste provided by this invention are selected from the group formed by vitamin A, vitamin B5, vitamin C, vitamin E and mixtures thereof.

In another particular embodiment of this invention, the formulation of presentation of the composition of the invention is an elixir or a colutory, preferably lacking alcohol, that contains the additives, suitable vehicles and excipients for the elaboration of said formulations of presentation. In a particular embodiment the colutory may be prepared extemporaneously maintaining the carbamide peroxide in solid form and adding water to the mixture in the quantity necessary when it is to be used.

The following examples serve to illustrate particular ways of realising the object of the present invention, although they should not be considered as limiting the scope thereof.

EXAMPLE 1

Preparation of a Bleaching Gel

A gel suitable for bleaching teeth with the following composition is prepared:

| Components | % by weight with respect to the total |
|---|---|
| Carbamide peroxide | 10 |
| Xylitol | 10 |
| Potassium citrate | 6.05 |
| Potassium fluoride | 0.45 |
| Carbopol ® 940 | 1.5 |
| Triethanolamine | 3.8 |
| Aroma | 1.5 |
| Saccharine | 0.1 |
| Glycerine | 66.6 |

For the preparation of said gel the quantities corresponding to each component are mixed. All the products used are commercial products.

By analogy other bleaching gels are prepared with 10% carbamide peroxide varying the quantities of carbopol® 940 (between 0.5 and 6% by weight) and triethanolamine (between 0 and 5% by weight).

EXAMPLE 2

Bleaching Gel with Carbamide Peroxide at 30%

Following the procedure described in Example 1 a gel is prepared suitable for bleaching teeth with carbamide peroxide at 30% that has the following composition

| Components | % by weight with respect to the total |
|---|---|
| Carbamide peroxide | 30 |
| Xylitol | 10 |

| Components | % by weight with respect to the total |
|---|---|
| Potassium citrate | 6.05 |
| Potassium fluoride | 0.45 |
| Carbopol ® 940 | 1.5 |
| Triethanolamine | 3.8 |
| Saccharine | 0.1 |
| Glycerine | 48.1 |

By analogy other bleaching gels are prepared with 30% carbamide peroxide varying the quantities of carbopol® 940 (between 0.5 and 6% by weight) and triethanolamine (between 0 and 5% by weight).

These gels are particularly suitable for topical application to dental pieces by means of a suitable utensil, such as a brush or a dental spatula, and are especially indicated for use by the professional in his or her practice with the aim of starting the dental bleaching treatment with splint or for acceleration of the process.

EXAMPLE 3

Bleaching Gel with Carbamide Peroxide at 12%

Following the procedure described in Example 1 a gel is prepared suitable for bleaching teeth with carbamide peroxide at 30% that has the following composition

| Components | % by weight with respect to the total |
|---|---|
| Carbamide peroxide | 12 |
| Xylitol | 10 |
| Potassium citrate | 6.05 |
| Potassium fluoride | 0.45 |
| Carbopol ® 940 | 1.5 |
| Triethanolamine | 3.8 |
| Aroma | 0.5 |
| Saccharine | 0.1 |
| Glycerine | 65.6 |

By analogy other bleaching gels are prepared with 12% carbamide peroxide varying the quantities of carbopol® 940 (between 0.5 and 6% by weight) and triethanolamine (between 0 and 5% by weight).

These gels are particularly suitable for use in daily brushing, for topical application to dental pieces using a suitable utensil, such as a brush or a dental spatula, as well as for use by the user on the splint prepared for the dental bleaching treatment.

EXAMPLE 4

Bleaching Gel with Carbamide Peroxide at 3%

Following the procedure described in Example 1 a gel is prepared suitable for bleaching teeth with carbamide peroxide at 3% that has the following composition

| Components | % by weight with respect to the total |
|---|---|
| Carbamide peroxide | 3 |
| Xylitol | 10 |
| Potassium citrate | 6.05 |

-continued

| Components | % by weight with respect to the total |
|---|---|
| Potassium fluoride | 0.45 |
| Carbopol ® 940 | 1.5 |
| Triethanolamine | 3.8 |
| Aroma | 0.5 |
| Saccharine | 0.1 |
| Glycerine | 74.6 |

By analogy other bleaching gels are prepared with 12% carbamide peroxide varying the quantities of carbopol® 940 (between 0.5 and 6% by weight) and triethanolamine (between 0 and 5% by weight).

These gels are particularly suitable for use in daily brushing of teeth in combination, preferably, with an appropriate whitening toothpaste, such as a toothpaste provided by this invention.

EXAMPLE 5

Preparation of a Whitening Toothpaste

A whitening toothpaste with the following composition was prepared:

| Components | % by weight with respect to total |
|---|---|
| Carbamide peroxide | 10 |
| Xylitol | 10 |
| Potassium salt | 6 |
| Fluoride salt | 0.45 |
| Sorbosil TC-15 | 13.8 |
| Sorbosil AC-30 | 4 |
| Titanium dioxide | 1 |
| Xanthane gum | 0.6 |
| Aroma | 0.9 |
| Colorant | 0.003 |
| Gemrall II | 0.1 |
| Saccharine | 0.1 |
| Glycerine | 53.047 |

By analogy another toothpaste was prepared with an identical composition to that mentioned above but adding Carbopol® 940 (0.5% by weight with respect to the total) and adding 52.527% by weight of glycerine.

The elaboration of both toothpastes was carried out mixing the different components by conventional techniques. The toothpastes obtained in both cases are especially indicated for dental bleaching.

EXAMPLE 6

Preparation of a Colutory

An oral colutory was prepared with the following composition:

| Components | % by weight with respect to total |
|---|---|
| Carbamide peroxide | 3 |
| Xylitol | 1 |
| Potassium salt | 0.6 |
| Fluoride salt | 0.45 |
| Alantoin | 0.2 |
| Saccharine | 0.02 |

-continued

| Components | % by weight with respect to total |
|---|---|
| Aroma | 0.1 |
| Colorant | 0.001 |
| Polyethyleneglycol (PEG 40) | 0.25 |
| Sodium Propylparaben | 0.06 |
| Sodium methylparaben | 0.12 |
| Water | 94.199 |

The elaboration of this oral colutory was carried out by mixing the different components using conventional techniques. The colutory obtained is suitable for dental bleaching.

What is claimed is:

1. An abrasive-free tooth bleaching gel, comprising:

| Components: | % by weight with respect to total: |
|---|---|
| Carbamide peroxide | 0.3–60 |
| Xylitol | 0.5–50 |
| Potassium citrate | 0.001–10 |
| Potassium fluoride | 0.15–3 |
| Gelling agent | 0.5–6 |
| Triethanolamine | 0.1–6 |
| Aroma | 0.5–6 |
| Saccharine | 0.1–6 |
| Glycerine | 45–75. |

2. A gel according to claim 1, which comprises:

| Components | % by weight, with respect to total |
|---|---|
| Carbamide peroxide | 30 |
| Xylitol | 10 |
| Potassium citrate | 6.05 |
| Potassium fluoride | 0.45 |
| Gelling agent | 0.5–6 |
| Triethanolamine | 0.1–6 |
| Saccharine | 0.1 |
| Glycerine | 48.1. |

3. A gel according to claim 1, which comprises:

| Components | % by weight, with respect to total |
|---|---|
| Carbamide peroxide | 12 |
| Xylitol | 10 |
| Potassium citrate | 6.05 |
| Potassium fluoride | 0.45 |
| Gelling agent | 0.5–6 |
| Triethanolamine | 0.1–6 |
| Aroma | 0.5 |
| Saccharine | 0.1 |
| Glycerine | 65.6. |

4. A gel according to claim 1, which comprises

| Components | % by weight, with respect to total |
|---|---|
| Carbamide peroxide | 3 |
| Xylitol | 10 |
| Potassium citrate | 6.05 |
| Potassium fluoride | 0.45 |

-continued

| Components | % by weight, with respect to total |
|---|---|
| Gelling agent | 0.5–6 |
| Triethanolamine | 0.1–6 |
| Aroma | 0.5 |
| Saccharine | 0.1 |
| Glycerine | 74.6. |

5. A method for bleaching teeth which comprises applying an effective quantity of a tooth bleaching gel according to claim 1 to the teeth to be bleached.

6. A method according to claim 5, which comprises preparing a splint that can be placed on the dental pieces to be bleached, applying a bleaching gel that contains between 10 and 15% by weight of carbamide peroxide to the inside of the splint, and placing the splint with the bleaching gel on the dental pieces to be bleached.

7. A method according to claim 5, which comprises applying an effective quantity of gel that contains between 20 and 50% by weight of carbamide peroxide to the external face of the denture or pieces to be bleached and leaving the gel to act for an appropriate period of time.

* * * * *